United States Patent
Poletti

(10) Patent No.: US 9,272,165 B2
(45) Date of Patent: Mar. 1, 2016

(54) COMPOSITION COMPRISING A SUCROSE ESTER AND A POLYGLYCEROL ESTER

(75) Inventor: Mickael Poletti, Paris (FR)

(73) Assignee: L'OREAL, Paris (FR)

( * ) Notice: Subject to any disclaimer, the term of this patent is extended or adjusted under 35 U.S.C. 154(b) by 420 days.

(21) Appl. No.: 12/706,902

(22) Filed: Feb. 17, 2010

(65) Prior Publication Data

US 2010/0215598 A1    Aug. 26, 2010

Related U.S. Application Data

(60) Provisional application No. 61/153,988, filed on Feb. 20, 2009.

(51) Int. Cl.
| | | |
|---|---|---|
| *A61K 8/02* | (2006.01) | |
| *A61Q 19/10* | (2006.01) | |
| *A61K 8/39* | (2006.01) | |
| *A61K 8/60* | (2006.01) | |
| *A61Q 1/14* | (2006.01) | |

(52) U.S. Cl.
CPC . *A61Q 19/10* (2013.01); *A61K 8/39* (2013.01); *A61K 8/60* (2013.01); *A61Q 1/14* (2013.01)

(58) Field of Classification Search
CPC ........... A61K 8/39; A61K 8/60; A61Q 19/10; A61Q 1/14
See application file for complete search history.

(56) References Cited

FOREIGN PATENT DOCUMENTS

| EP | 0 289 636 | 11/1988 | |
|---|---|---|---|
| EP | 1 679 063 | 7/2006 | |
| EP | 1 902 633 | 3/2008 | |
| EP | 2022469 A1 * | 2/2009 | ............... A61K 8/34 |
| JP | 58-103325 | 6/1983 | |
| JP | 2005-68083 A | 3/2005 | |
| WO | WO 2008/140065 | 11/2008 | |

OTHER PUBLICATIONS

Database WPI Week 199605, Thomson Scientific, London, GB; AN 1996-044286, XP002549513, and JP 07 308562 (Mitsubishi Chem Corp). Nov. 28, 1995.
Japanese Office Action issued May 26, 2014 in Patent Application No. 2010-029249.
Office Action in the corresponding Japanese Patent Application No. 2010-029249 dated Mar. 23, 2015 (English Translation Only).

* cited by examiner

*Primary Examiner* — Lezah Roberts
*Assistant Examiner* — Nannette Holloman
(74) *Attorney, Agent, or Firm* — Oblon, McClelland, Maier & Neustadt, L.L.P.

(57) ABSTRACT

Composition containing an aqueous phase, a lipophilic compound and an emulsifying system containing a fatty acid ester of sucrose and a fatty acid ester of polyglycerol, and to its use in the cosmetics field, in particular for cleansing and/or for removing makeup from keratin materials.

18 Claims, No Drawings

COMPOSITION COMPRISING A SUCROSE ESTER AND A POLYGLYCEROL ESTER

REFERENCE TO PRIOR APPLICATIONS

This application claims priority to U.S. provisional application Ser. No. 61/153,988, filed Feb. 20, 2009; and is related to French patent application 09 50930, filed Feb. 13, 2009, both incorporated herein by reference.

FIELD OF THE INVENTION

The present invention relates to a composition comprising a lipophilic compound and an emulsifying system comprising a fatty acid ester of sucrose and a fatty acid ester of polyglycerol, and to the use thereof in the cosmetics field, in particular for cleansing and/or for removing makeup from keratin materials.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

To obtain satisfactory working properties and/or good product performance, it is common practice to introduce into aqueous cosmetic compositions water-immiscible ingredients, for instance fragrance, essential oils, lipophilic active agents, sunscreens or fatty substances.

However, due to their lipophilic nature, certain compounds are more or less difficult to dissolve in these formulations, and surface leaching may take place during storage. Such a phenomenon is undesirable from the point of view of stability of the formulation and/or with regard to consumer comfort insofar as it may destabilize the composition and/or affect the aesthetic appearance of the product (cloudy appearance) and/or give rise to unpleasant cosmetic results when applied to the skin and/or the hair; this phenomenon also limits the concentration of active agents in these formulations, which does not make it possible to obtain sufficiently effective products.

In order to dissolve and stabilize these lipophilic compounds, it is known practice to use oxyethylenated surfactants partly derived from petrochemistry (for example oxyethylenated hydrogenated castor oil).

However, consumers are increasingly in search of cosmetic products that are formed, totally or partly, from natural constituents or constituents of natural origin.

The term "natural compound" means a compound that is obtained directly from the earth or the soil, or from plants or animals, via, where appropriate, one or more physical processes, for instance grinding, refining, distillation, purification or filtration.

The term "compound of natural origin" means a natural compound that has undergone one or more additional chemical or industrial treatments, giving rise to modifications that do not affect the essential qualities of this compound and/or a compound predominantly comprising natural constituents that may or may not have undergone transformations as indicated above.

As non-limiting examples of additional chemical or industrial treatments giving rise to modifications that do not affect the essential qualities of a natural compound, mention may be made of those permitted by the control authorities such as Ecocert (Frame of reference for cosmetic, biological and ecological products, January 2003) or defined in manuals recognized in the field, such as the *Cosmetics and Toiletries Magazine*, 2005, vol. 120, 9:10.

There is thus still a need for a system for dissolving lipophilic compounds that is compatible with the formulation of "natural" or "bio-certified" cosmetic products, which allows these lipophilic compounds to be formulated without any concentration limit, so as to obtain stable, efficient formulations that are pleasant to use and that have an attractive aesthetic appearance, especially a clear, non-cloudy appearance. The inventor has discovered that a surfactant system comprising a combination of a fatty acid ester of sucrose and a fatty acid ester of polyglycerol can achieve the above objectives.

DETAILED DESCRIPTION OF THE PREFERRED EMBODIMENTS

One subject of the present invention is a composition comprising an aqueous phase, at least one lipophilic compound and the combination of at least one fatty acid ester of sucrose and of at least one fatty acid ester of polyglycerol, preferably as the main surfactant system of the composition, the ratio of fatty acid ester of sucrose to fatty acid ester of polyglycerol being greater than or equal to 0.06.

The composition according to the invention preferably has a clear or translucent appearance, while at the same time being stable and comfortable on application.

The composition according to the invention is preferably intended for topical application and thus preferably contains a physiologically acceptable medium. The term "physiologically acceptable medium" means herein a medium that is compatible with keratin materials such as the skin, mucous membranes, the scalp, the eyes and/or keratin fibres such as the eyelashes or the hair.

Lipophilic Compound

The term "lipophilic compound" means any water-immiscible cosmetic or dermatological organic compound that may be completely dissolved in molecular form in a liquid fatty phase, or that may be dissolved in colloidal form (for example in micellar form) in a liquid fatty phase.

Examples of lipophilic compounds that may be mentioned include antibacterial agents, antifungal agents, anti-seborrhoeic agents, antiacne agents, keratolytic agents, cicatrizing agents, pigmentation modifiers, tanning accelerators, artificial tanning agents, liporegulators, anti-ageing and anti-wrinkle agents, emollients, refreshing agents, vascular protectors, insect repellents, deodorants, antidandruff agents, hair-loss counteractants, essential oils, fragrances, sunscreens, antioxidants, free-radical scavengers, moisturizers, or fatty substances that are liquid at room temperature (oils), fatty substances that are solid at room temperature (waxes) or fatty substances that are semi-solid at room temperature, such as pasty fatty substances or butters.

Examples of lipophilic compounds that may especially be mentioned include:
  ceramides,
  essential fatty acids,
  vitamins such as vitamin A (retinol) or esters thereof, vitamin E or esters thereof such as tocopheryl acetate, vitamin D or derivatives thereof and vitamin F or derivatives thereof, carotenes such as β-carotene and derivatives thereof such as lycopene, salicylic acid derivatives, especially those described in documents FR-A-2 581 542, EP-A-378 936 and EP-A-570 230, lipophilic sunscreens, for instance triazine derivatives, dibenzoyl methane derivatives or benzophenones, essential oils, which may be chosen especially from eucalyptus oil, lavandin oil, lavender oil, vetiver oil, Litsea cubeba oil, lemon oil, orange oil, sandalwood oil, rosemary oil, camomile oil, savory oil, nutmeg oil, cinnamon oil, hyssop oil, caraway oil, mandarin oil, juniper oil, clove oil, bergamot oil, geranium oil, cade oil, ginger oil, carrot oil, lemon grass oil, rose oil, fennel oil, thyme oil and peppermint oil, and mixtures thereof.

As oils that may be used in the composition of the invention, mention may be made, for example, of:

hydrocarbon-based oils of animal origin, such as perhydrosqualene;

hydrocarbon-based oils of plant origin, such as liquid triglycerides of fatty acids of 4 to 30 carbon atoms, such as heptanoic or octanoic acid triglycerides or alternatively, for example, jojoba oil, babassu oil, sunflower oil, olive oil, coconut oil, Brazil nut oil, marula oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides such as those sold by the company Stéarineries Dubois or those sold under the names Miglyol 810, 812 and 818 by the company Dynamit Nobel, or shea butter oil;

synthetic esters and ethers in particular of fatty acids, such as the oils of formulae $R_1COOR_2$ and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, such as, for example, purcellin oil, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, petroleum jelly, polydecenes, isohexadecane, isododecane or hydrogenated polyisobutene such as Parleam Oil®;

silicone oils such as volatile or non-volatile polydimethylsiloxanes (PDMSs) containing a linear or cyclic silicone chain, which are liquid or pasty at room temperature, especially volatile silicone oils, in particular cyclopolydimethylsiloxanes (cyclomethicones) such as cyclohexadimethylsiloxane and cyclopenta-dimethylsiloxane; polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethyl-siloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

Mention may be made in particular of oils chosen from:

esters derived from the reaction of at least one fatty acid containing at least 6 carbon atoms, preferably from 6 to 26 carbon atoms, better still from 6 to 20 carbon atoms and even better still from 6 to 16 carbon atoms, and of at least one alcohol containing from 1 to 17 carbon atoms and better still from 3 to 15 carbon atoms; mention may be made especially of isopropyl myristate, isopropyl palmitate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols containing 12 or 13 carbon atoms, dicaprylyl carbonate, such as the product sold under the name Cetiol CC by the company Cognis, fatty acid ethers containing from 6 to 20 carbon atoms such as dicaprylyl ether (Cetiol OE from Cognis), glyceryl ethers containing from 6 to 12 carbon atoms, for instance 2-ethylhexyl glyceryl ether (INCI name: ethylhexylglycerin), such as Sensiva SC 50 from the company Schulke & Mayr GmbH, volatile linear alkanes, advantageously of plant origin, containing from 7 to 17 carbon atoms, in particular from 9 to 15 carbon atoms and more particularly from 11 to 13 carbon atoms. As examples of volatile linear alkanes that are suitable for use in the invention, mention may be made of those described in the patent application from the company Cognis, WO 2007/068 371. As examples of volatile linear alkanes that are suitable for use in the invention, mention may be made of n-nonane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$), n-hexadecane ($C_{16}$) and n-heptadecane ($C_{17}$), and mixtures thereof.

According to one embodiment, use will be made of a mixture of undecane ($C_{11}$) and of tridecane ($C_{13}$) prepared according to examples 1 and 2 of the WO2008/155059 application by Cognis.

According to one embodiment, use will be made of n-dodecane ($C_{12}$) or n-tetradecane ($C_{14}$) sold by SASOL respectively under the trade names PARAFOL 12-97 and PARAFOL 14-97, and mixtures thereof.

Preferably, the oil is chosen from oils of plant origin.

The fatty substances that are semi-solid at room temperature, such as pasty fatty substances or butters, may be hydrocarbon-based compounds of plant origin, such as liquid triglycerides of fatty acids containing from 4 to 30 carbon atoms. Examples that may be mentioned include shea butter and cocoa butter.

In particular, the lipophilic compound may be chosen from fragrances, essential oils, oils of plant origin, pasty fatty substances and butters such as those mentioned above, and mixtures thereof, in particular from essential oils and oils of plant origin.

The lipophilic compound may be present in a content ranging for example from 0.001% to 40% by weight, preferably from 0.01% to 30% by weight and better still from 0.05% to 20% by weight, relative to the total weight of the composition.

In particular, when the lipophilic compound is chosen from essential oils, oils of plant origin, pasty fatty substances and butters, it may be present in the composition in a content ranging from 0.001% to 5% by weight, preferably from 0.01% to 2% by weight and better still from 0.05% to 1% by weight relative to the total weight of the composition.

Fatty Acid Ester of Sucrose

According to the present invention, the fatty acid ester of sucrose is preferably chosen from esters derived from the reaction of sucrose(s) (saccharose) and of fatty acid(s) containing from 10 to 24 carbon atoms, preferably from 12 to 20 carbon atoms, better still from 12 to 18 carbon atoms and even better still from 12 to 16 carbon atoms.

The fatty acids containing from 10 to 24 carbon atoms may be linear or branched, and saturated or unsaturated.

The fatty acids may be chosen from oleic acid, lauric acid, palmitic acid, myristic acid, stearic acid, linoleic acid and capric acid, or mixtures thereof.

According to one embodiment, the fatty acid ester of sucrose is chosen from esters derived from the reaction of sucrose and a fatty acid containing from 12 to 18 carbon atoms and preferably from 12 to 16 carbon atoms, such as lauric acid and/or palmitic acid, for instance sucrose laurate or sucrose palmitate, or a mixture thereof.

The fatty acid esters of sucrose may be chosen from mono-, di-, tri- and tetra-esters, and polyesters, and mixtures thereof. Esters with a low degree of esterification are preferably used, for instance fatty acid monoesters, diesters or triesters of sucrose, or a mixture thereof. The fatty acid ester of sucrose may be in the form of a mixture of esters with a low degree of esterification, for instance a mixture of monoester and diester or a mixture of monoester, diester and triester.

When a mixture of fatty acid esters of sucrose is used, a preferred mixture is one in which the esters with a low degree of esterification, in particular monoesters, are predominant and represent, for example, at least 50% and preferably at least 60% by weight of the mixture of fatty acid esters of sucrose.

It is in particular possible to use a mixture of esters of sucrose and of fatty acids containing from 12 to 16 carbon atoms, in particular a mixture of mono-, di- and triesters of lauric acid or of palmitic acid, the said mixture possibly comprising in minor amount (in a content of less than or equal to 40% by weight relative to the weight of the mixture of fatty acid esters of sucrose) esters of sucrose and of fatty acids in which the fatty acid contains more than 16 carbon atoms.

Preferably, the fatty acid ester of sucrose used in the present invention has an HLB of greater than or equal to 10 and preferably greater than or equal to 12.

As is well known, the term HLB (hydrophilic-lipophilic balance) means the equilibrium between the size and force of the hydrophilic group and the size and force of the lipophilic group of the surfactant.

The Griffin HLB value is defined in J. Soc. Cosm. Chem. 1954 (volume 5), pages 249-256.

Examples of esters or mixtures of esters of sucrose and of fatty acid that may be mentioned include:
  Surfhope SE Cosme C-1416, with an HLB value of 16, which is a sucrose myristate comprising about 80% monoester, the rest of the mixture being composed of di- and triesters,
  Surfhope SE Cosme C-1216, the INCI name of which is sucrose laurate, with an HLB value of 16, and which comprises about 75% to 90% monoester, the rest of the mixture being composed of di- and triesters,
  Surfhope SE Cosme C-1215L, the INCI name of which is sucrose laurate, with an HLB value equal to 15, comprising about 70% monoesters, the rest of the mixture being composed of diesters and other polyesters,
  Surfhope SE Cosme C-1616, with an HLB value of 16, which is a mixture of esters of sucrose and of palmitic and/or stearic acid (INCI name: sucrose palmitate), comprising from 75% to 90% monoester, the rest of the mixture being composed of di- and triesters, and possibly comprising sucrose stearate and sucrose palmitate stearate.
Mention may also be made of the ester bearing the INCI name sucrose laurate, sold by the company Dai-Ichi Seiyaku under the reference DK Ester S-L18A, with an HLB value equal to 17, comprising 70% monoesters and 30% di- and triesters.

As examples of esters or mixtures of esters of sucrose and of fatty acid, mention may also be made of:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% di-tri-ester-polyester;
  the sucrose mono-dipalmito-stearate sold by the company Goldschmidt under the name Tegosoft® PSE.

The amount of fatty acid ester(s) of sucrose may range, for example, from 0.1% to 20% by weight, preferably from 0.2% to 15% by weight, better still from 0.5% to 10% by weight and even better still from 1% to 5% by weight relative to the total weight of the composition.

Fatty Acid Ester of Polyglycerol

According to the present invention, the fatty acid ester of polyglycerol is preferably chosen from esters derived from the reaction of polyglycerol comprising from 2 to 12 glycerol units and preferably from 3 to 10 glycerol units and of at least one fatty acid containing from 8 to 24 carbon atoms, preferably from 8 to 20 carbon atoms, better still from 10 to 18 carbon atoms and even better still from 10 to 14 carbon atoms.

The fatty acids containing from 8 to 24 carbon atoms may be linear or branched, and saturated or unsaturated.

The fatty acids may be chosen from oleic acid, stearic acid, isostearic acid, lauric acid, palmitic acid, myristic acid, linoleic acid, capric acid and caprylic acid, or mixtures thereof.

The fatty acid esters of polyglycerol may be chosen from mono-, di-, tri- and tetra-esters, and polyesters, and mixtures thereof. Esters with a low degree of esterification, for instance fatty acid monoesters, diesters or triesters of sucrose, or a mixture thereof, are preferably used. The fatty acid ester of polyglycerol may be in the form of a mixture of esters with a low degree of esterification, for instance a mixture of monoester and diester or a mixture of monoester, diester and triester.

According to one preferred embodiment, a fatty acid ester of polyglycerol chosen from esters derived from the reaction of polyglycerol comprising from 2 to 12 glycerol units and preferably from 4 to 10 glycerol units, and of at least one fatty acid comprising less than 16 carbon atoms and preferably less than 15 carbon atoms, for example from 8 to 16 carbon atoms and better still from 8 to 14 carbon atoms, is used.

According to one embodiment, the fatty acid ester of polyglycerol is chosen from esters derived from the reaction of polyglycerol comprising from 4 to 10 glycerol units and of at least one fatty acid containing from 8 to 12 carbon atoms and preferably from 10 to 12 carbon atoms, such as lauric acid and/or capric acid. Mention may be made, for example, of the ester derived from the reaction of polyglycerol-10 (glycerol homopolymer comprising 10 glycerol units) and of lauric acid (INCI name: polyglyceryl-10 laurate), such as the product sold by the company Dr Straetmans under the reference Dermofeel G 10 L, and the ester derived from the reaction of polyglycerol-4 (glycerol homopolymer comprising 4 glycerol units) and of capric acid (INCI name: polyglyceryl-4 caprate), such as the product sold by the company Evonik under the reference Tegosoft PC 41.

The amount of fatty acid ester(s) of polyglycerol may range, for example, from 0.1% to 20% by weight, preferably from 0.2% to 15% by weight, better still from 0.5% to 10% by weight and even better still from 1% to 5% by weight relative to the total weight of the composition.

The ratio of fatty acid ester of sucrose to fatty acid ester of polyglycerol is greater than or equal to 0.06, preferably greater than or equal to 0.5 and better still greater than or equal to 0.9. It may range, for example, from 0.06 to 100, better still from 0.5 to 50 and even better still from 0.9 to 2 and may in particular be of the order of 1. All values and subranges within these ranges are specifically included as if explicitly written out such as, for example, 0.6, 0.8, 1.2, 1.4, 1.6, 1.8, 3, 10, 20, 30, etc.

The combination of fatty acid ester of sucrose and fatty acid ester of polyglycerol constitutes the main non ionic surfactant system of the composition.

The term "main non ionic surfactant system" means a system which, in its absence, does not lead to the formation of a stable composition, i.e. the other non ionic surfactants (different from the fatty acid ester of sucrose and fatty acid ester of polyglycerol) that the composition may contain do not lead alone to the a stable composition in the absence of said esters.

The term "stable" means a composition which, either just after having been formulated, or after having been placed, on the one hand, in an oven at 45° C. and, on the other hand, in a refrigerator at 4° C., for two months, does not, after returning to room temperature, show any phase separation of the aqueous and fatty phases, or any leaching of fatty phase at the surface or any cloudiness (if the composition is clear).

According to a specific embodiment, the combination of fatty acid ester of sucrose and fatty acid ester of polyglycerol constitutes the main surfactant system of the composition.

The term "main surfactant system" means a system which, in its absence, does not lead to the formation of a stable composition.

According to one particular embodiment, the composition comprises less than 1% of additional non ionic surfactant (limits inclusive) and better still less than 0.5% of additional non ionic surfactant (limits inclusive). The term "additional non ionic surfactant" means a surfactant different from the fatty acid ester of sucrose and fatty acid ester of polyglycerol.

According to one particular embodiment, the composition is free of additional non ionic surfactant.

According to one particular embodiment, the composition comprises less than 1% of additional surfactant (limits inclusive) and better still less than 0.5% of additional (limits inclusive).

The term "additional surfactant" means all type of surfactant, different from the fatty acid ester of sucrose and fatty acid ester of polyglycerol, including the foaming surfactant.

According to one particular embodiment, the combination of fatty acid ester of sucrose and fatty acid ester of polyglycerol constitutes the sole surfactant system of the composition, i.e. the composition is free of additional surfactant.

According to one embodiment, the composition may comprise at least one foaming agent. As regards the definition of this compound, reference may be made to Kirk-Othmer's "Encyclopaedia of Chemical Technology", volume 22, pages 333-432, 3rd edition, 1979, published by Wiley, in which are mentioned the main classes of foaming agents known to those skilled in the art, and also their function, in particular their foaming nature. These foaming agents are different from the surfactants of the main surfactant system and from the stabilizing or emulsifying surfactants in so far as they afford the composition a foaming function. Preferably they do not by themselves have any influence on the stabilization of the composition.

The foaming agents may be present in the composition according to the invention in a content ranging for example from 0.1% to 30% by weight, preferably from 0.1% to 20% by weight and better still from 0.5% to 15% by weight relative to the total weight of the composition.

They may be chosen from anionic, cationic, amphoteric or zwitterionic foaming agents and mixture thereof.

The anionic surfactants may be chosen especially from anionic derivatives of proteins of plant origin or of silk proteins, phosphates and alkyl phosphates, carboxylates, sulfosuccinates, amino acid derivatives, alkyl sulfates, alkyl ether sulfates, sulfonates, isethionates, taurates, alkyl sulfoacetates, polypeptides and anionic derivatives of alkyl-polyglucosides, and mixtures thereof.

1) The anionic derivatives of proteins of plant origin are protein hydrolysates containing a hydrophobic group, the said hydrophobic group possibly being naturally present in the protein or being added by reacting the protein and/or the protein hydrolysate with a hydrophobic compound. The proteins are of plant origin or derived from silk, and the hydrophobic group may especially be a fatty chain, for example an alkyl chain containing from 10 to 22 carbon atoms. As anionic derivatives of proteins of plant origin, mention may be made more particularly of protein hydrolysates of apple, wheat, soybean or oat, comprising an alkyl chain containing from 10 to 22 carbon atoms, and salts thereof. The alkyl chain can be in particular a lauryl chain and the salt can be a sodium, potassium and/or ammonium salt.

Thus, as protein hydrolysates containing a hydrophobic group, mention may be made, for example, of salts of hydrolysates of silk protein modified with lauric acid, such as the product sold under the name Kawa Silk by the company Kawaken; salts of hydrolysates of wheat protein modified with lauric acid, such as the potassium salt sold under the name Aminofoam W OR by the company Croda (INCI name: potassium lauroyl wheat amino acids) and the sodium salt sold under the name Proteol LW 30 by the company SEPPIC (INCI name: sodium lauroyl wheat amino acids); salts of hydrolysates of oat protein comprising an alkyl chain containing from 10 to 22 carbon atoms and more especially salts of hydrolysates of oat protein modified with lauric acid, such as the sodium salt sold under the name Proteol Oat (aqueous 30% solution) by the company SEPPIC (INCI name: sodium lauroyl oat amino acids); salts of hydrolysates of apple protein, comprising an alkyl chain containing from 10 to 22 carbon atoms, such as the sodium salt sold under the name Proteol APL (30% water-glycol solution) by the company SEPPIC (INCI name: sodium cocoyl apple amino acids). Mention may also be made of the mixture of lauroyl amino acids (aspartic acid, glutamic acid, glycine and alanine) neutralized with sodium N-methylglycinate, sold under the name Proteol SAV 50 S by the company SEPPIC (INCI name: sodium cocoyl amino acids).

2) Phosphates and alkyl phosphates that may be mentioned, for example, include monoalkyl phosphates and dialkyl phosphates, such as the lauryl monophosphate sold under the name MAP 20® by the company Kao Chemicals, the potassium salt of dodecylphosphoric acid, as a mixture of monoester and diester (mainly diester), sold under the name Crafol AP-31® by the company Cognis, the mixture of monoester and diester of octylphosphoric acid, sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium salt or triethanolamine salt of monoalkyl (C12-C13) phosphate sold under the references Arlatone MAP 230K-40® and Arlatone MAP 230T-60® by the company Uniqema, and the potassium lauryl phosphate sold under the name Dermalcare MAP XC-99/09® by the company Rhodia Chimie, and the potassium cetyl phosphate sold under the name Arlatone MAP 160K by the company Uniqema.

3) Carboxylates that may be mentioned include:
amido ether carboxylates (AEC), for instance sodium laurylamido ether carboxylate (3 EO) sold under the name Akypo Foam 30® by the company Kao Chemicals;
polyoxyethylenated carboxylic acid salts, for instance oxyethylenated (6 EO) sodium lauryl ether carboxylate (65/25/10 $C_{12\text{-}14\text{-}16}$) sold under the name Akypo Soft 45 NV® by the company Kao Chemicals; polyoxyethylenated and carboxymethylated fatty acids of olive oil origin sold under the name Olivem 400® by the company Biologia E Technologia; oxyethylenated (6 EO) sodium tridecyl ether carboxylate sold under the name Nikkol ECTD-6NEX® by the company Nikkol;
fatty acid salts containing a $C_6$ to $C_{22}$ alkyl chain, neutralized with an organic or mineral base, which constitute soaps. The fatty acid salt or soap is obtained from a fatty acid and a base, the fatty acid comprising a linear or branched, saturated or unsaturated alkyl chain containing from 12 to 22 carbon atoms and preferably 12 to 20 carbon atoms. The bases (also known as saponifying agents) totally or partially neutralize the fatty acids. The bases that may be used to obtain the salts may be, for example, mineral bases, for instance alkali metal hydroxides (sodium hydroxide and potassium hydroxide), alkaline-earth metal (magnesium) hydroxides or ammonium hydroxide, or alternatively organic bases such as triethanolamine, N-methylglucamine, lysine and arginine. The fatty acid may be chosen in particular from $C_{10}$ to $C_{24}$ and especially $C_{12}$-$C_{18}$ fatty acids, and in particular lauric acid, myristic acid, stearic acid or palmitic acid, and mixtures thereof.

The soap is generally introduced into a second composition in the form of the base, on the one hand, and of the fatty acid, on the other hand, the formation of the salt taking place in situ.

4) Amino acid derivatives that may especially be mentioned include alkaline salts of amino acids, such as:
sarcosinates, for instance sodium lauroyl sarcosinate sold under the name Sarkosyl NL 97® by the company Ciba or sold under the name Oramix L 30® by the company SEPPIC, sodium myristoyl sarcosinate sold under the name Nikkol Sarcosinate MN® by the company Nikkol, or sodium palmitoyl sarcosinate sold under the name Nikkol Sarcosinate PN® by the company Nikkol;
alaninates, for instance the sodium N-lauroyl-N-methylamidopropionate sold under the name Sodium Nikkol Alaninate LN 30® by the company Nikkol or sold under the name Alanone ALE® by the company Kawaken, and the triethanolamine N-lauroyl-N-methylalanine sold under the name Alanone Alta® by the company Kawaken;
glutamates, for instance the triethanolamine monococoylglutamate sold under the name Acylglutamate CT-12® by the company Ajinomoto and the triethanolamine lauroylglutamate sold under the name Acylglutamate LT-12® by the company Ajinomoto;
aspartates, for instance the mixture of triethanolamine N-lauroyl aspartate and of triethanolamine N-myristoyl aspartate, sold under the name Asparack® by the company Mitsubishi;
glycine derivatives (glycinates), for instance the sodium N-cocoylglycinate sold under the names Amilite GCS-12® and Amilite GCK 12 by the company Ajinomoto;
citrates, such as the oxyethylenated (9 mol) citric monoester of cocoyl alcohols sold under the name Witconol EC 1129 by the company Goldschmidt;
galacturonates, such as the sodium dodecyl-D-galactoside uronate sold by the company Soliance.

5) Examples of sulfosuccinates that may be mentioned include the oxyethylenated (3 EO) lauryl monosulfosuccinate (70/30 C12/C14) sold under the names Setacin 103 Special® and Rewopol SB-FA 30 K 4® by the company Witco, the disodium salt of a C12-C14 alkyl hemisulfosuccinate, sold under the name Setacin F Special Paste® by the company Zschimmer Schwarz, the oxyethylenated (2 EO) disodium oleamidosulfosuccinate sold under the name Standapol SH 135® by the company Cognis, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S1333® by the company Witco. Polydimethylsiloxane sulfosuccinates may also be used, such as disodium PEG-12 dimethicone sulfosuccinate sold under the name Mackanate-DC30 by the company MacIntyre.

6) Examples of alkyl sulfates that may be mentioned include triethanolamine lauryl sulfate (INCI name: TEA-lauryl sulfate) such as the product sold by the company Huntsman under the name Empicol TL40 FL or the product sold by the company Cognis under the name Texapon T42, which are products in the form of an aqueous 40% solution. Mention may also be made of ammonium lauryl sulfate (CTFA name: ammonium lauryl sulfate), such as the product sold by the company Huntsman under the name Empicol AL 30FL, which is an aqueous 30% solution.

7) Examples of alkyl ether sulfates that may be mentioned include sodium lauryl ether sulfate (INCI name: sodium laureth sulfate), for instance the product sold under the names Texapon N40 and Texapon AOS 225 UP by the company Cognis or the product sold under the name Empicol ESB 3/FL3 by the company Huntsman, and ammonium lauryl ether sulfate (INCI name: ammonium laureth sulfate), for instance the product sold under the name Standapol EA-2 by the company Cognis.

8) Examples of sulfonates that may be mentioned include α-olefin sulfonates, for instance the sodium α-olefin sulfonate (C14-16) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the sodium secondary olefin sulfonate sold under the name Hostapur SAS 30® by the company Clariant; linear alkyl aryl sulfonates, for instance the sodium xylenesulfonate sold under the names Manrosol SXS30®, Manrosol SXS40® and Manrosol SXS93® by the company Manro.

9) Isethionates that may be mentioned include acylisethionates, for instance sodium cocoylisethionate, such as the product sold under the name Jordapon CI P® by the company Jordan.

10) Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

11) The anionic derivatives of alkylpolyglucosides may be, in particular, glyceryl ethers, carbonates, sulfosuccinates, tartrates and citrates obtained from alkylpolyglucosides. Mention may be made, for example, of the sodium salt of cocoylpolyglucoside (1,4) tartaric ester, sold under the name Eucarol AGE-ET® by the company Cesalpinia, the disodium salt of cocoylpolyglucoside (1,4) sulfosuccinic ester, sold under the name Essai 512 MP® by the company SEPPIC, and the sodium salt of cocoylpolyglucoside (1,4) citric ester, sold under the name Eucarol AGE-EC® by the company Cesalpinia.

Amphoteric and Zwitterionic Foaming Agents

They may be chosen, for example, from betaines, N-alkylamidobetaines and derivatives thereof, sultaines, alkyl polyaminocarboxylates and alkylampho-acetates, and mixtures thereof.

1) Betaines that may be mentioned especially are alkylbetaines, for example cocobetaine, for instance the product sold under the name Dehyton AB-30® by the company Cognis, laurylbetaine, for instance the product sold under the name Genagen KB® by the company Clariant, oxyethylenated (10 EO) laurylbetaine, for instance the product sold under the name Lauryl Ether (10 EO) Betaine® by the company Shin Nihon Rica, and oxyethylenated (10 EO) stearylbetaine, for instance the product sold under the name Stearyl Ether (10 EO) Betaine® by the company Shin Nihon Rica.

Among the N-alkylamidobetaines and derivatives thereof that may be mentioned, for example, are the cocamidopropylbetaine sold under the name Lebon 2000 HG® by the company Sanyo, or sold under the name Empigen BB® by the company Albright & Wilson, and the lauramidopropyl betaine sold under the name Rewoteric AMB12P® by the company Witco.

2) Sultaines that may be mentioned include hydroxylsultaines, such as cocoylamidopropylhydroxy-sultaine, for instance the product sold under the name Rewoteric AM CAS by the company Goldschmidt-Degussa, or the product sold under the name Crosultaine C-50® by the company Croda.

3) Alkyl polyaminocarboxylates (APACs) that may be mentioned include the sodium cocoylpolyaminocarboxylate sold under the name Ampholak 7 CX/C® and Ampholak 7 CX® by the company Akzo Nobel, the sodium stearylpolyamidocarboxylate sold under the name Ampholak 7 TX/C by the company Akzo Nobel and the sodium carboxymethyloleylpolypropylamine sold under the name Ampholak XO7/C® by the company Akzo Nobel.

4) Alkylamphoacetates that may be mentioned, for example, include N-disodium N-cocoyl-N-carboxymethoxyethyl-N-carboxymethylethylenediamine (INCI name: disodium cocoamphodiacetate), for instance the product sold under the name Miranol C2M Concentré NP® by the company Rhodia, and N-sodium N-cocoyl-N-hydroxyethyl-N-carboxymethylethylenediamine (INCI name: sodium cocoamphoacetate), and sodium cocoamphohydroxypropyl sulfonate sold under the name Miranol CSE by the company Rhodia.

Cationic Foaming Agents

The cationic foaming agents that may be used according to the present invention are especially optionally polyoxyalkylenated salts of primary, secondary or tertiary fatty amines; quaternary ammonium salts; imidazoline derivatives; amine oxides of cationic nature, and/or a mixture thereof.

Examples of quaternary ammonium salts include:

those of general formula (IV) below:

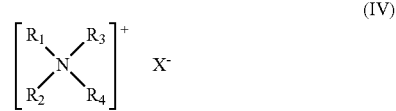

in which the radicals $R_1$ to $R_4$, which may be identical or different, represent a linear or branched aliphatic radical containing from 1 to 30 carbon atoms, or an aromatic radical such as aryl or alkylaryl. The aliphatic radicals can comprise heteroatoms such as, in particular, oxygen, nitrogen, sulfur or halogens. The aliphatic radicals are chosen, for example, from alkyl, alkoxy, polyoxy($C_2$-$C_6$)alkylene, alkylamide, ($C_{12}$-$C_{22}$)alkylamido ($C_2$-$C_6$)alkyl, ($C_{12}$-$C_{22}$)alkylacetate and hydroxyalkyl radicals, comprising from about 1 to 30 carbon atoms; $X^-$ is an anion chosen from the group of halides, phosphates, acetates, lactates, ($C_2$-$C_6$)alkyl sulfates and alkyl or alkylaryl sulfonates. Preferably, $R_1$ and $R_2$ denote a $C_1$-$C_4$ alkyl or a $C_1$-$C_4$ hydroxyalkyl;

quaternary ammonium salts of imidazolinium, for instance the salt of formula (V) below:

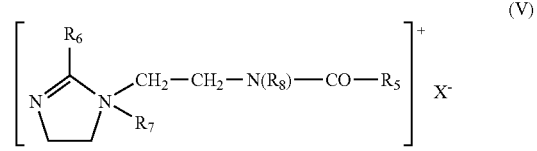

in which $R_5$ represents an alkenyl or alkyl radical containing from 8 to 30 carbon atoms, for example tallow fatty acid derivatives, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, $X^-$ is an anion chosen from the group of halides, phosphates, acetates, lactates, alkyl sulfates and alkyl or alkylaryl sulfonates. $R_5$ and $R_6$ preferably denote a mixture of alkenyl or alkyl radicals containing from 12 to 21 carbon atoms, for example tallow fatty acid derivatives, $R_7$ denotes a methyl radical and $R_8$ denotes a hydrogen atom;

diquaternary ammonium salts of formula (VI):

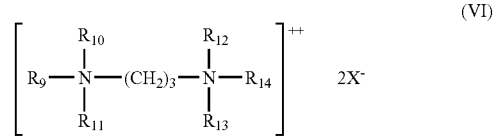

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen or an alkyl radical containing from 1 to 4 carbon atoms, and $X^-$ is an anion chosen from the group of halides, acetates, phosphates, nitrates and methyl sulfates;

quaternary ammonium salts containing at least one ester function, for example those of formula (VII) below:

$$R_{17}-\overset{O}{\underset{\|}{C}}-(OC_nH_{2n})_y-\underset{\underset{R_{15}}{|}}{\overset{(C_rH_{2r}O)_z-R_{18}}{\overset{|}{N^+}}}-(C_pH_{2p}O)_x-R_{16} \quad X^-, \quad (VII)$$

in which:

$R_{15}$ is chosen from $C_1$-$C_6$ alkyl radicals and $C_1$-$C_6$ hydroxyalkyl or dihydroxyalkyl radicals;

$R_{16}$ is chosen from:
a radical $$R_{19}-\overset{O}{\underset{\|}{C}}-$$

linear or branched, saturated or unsaturated $C_1$-$C_{22}$ hydrocarbon-based radicals $R_{20}$,
a hydrogen atom,
$R_{18}$ is chosen from:
a radical $$R_{21}-\overset{O}{\underset{\|}{C}}-$$

linear or branched, saturated or unsaturated $C_1$-$C_6$ hydrocarbon-based radicals $R_{22}$,
a hydrogen atom, $R_{17}$, $R_{19}$ and $R_{21}$, which may be identical or different, are chosen from linear or branched, saturated or unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{16}$ denotes $R_{20}$ and that when z is 0, then $R_{18}$ denotes $R_{22}$.

The $R_{15}$ alkyl radicals may be linear or branched and more particularly linear.

$R_{15}$ preferably denotes a methyl, ethyl, hydroxyethyl or dihydroxypropyl radical and more particularly a methyl or ethyl radical.

The sum x+y+z is advantageously from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it preferably contains 1 to 3 carbon atoms.

$R_{17}$, $R_{19}$ and $R_{21}$, which may be identical or different, are advantageously chosen from linear or branched, saturated or unsaturated $C_{11}$-$C_{21}$ hydrocarbon-based radicals, and more particularly from linear or branched, saturated or unsaturated, $C_{11}$-$C_{21}$ alkyl and alkenyl radicals.

x and z, which may be identical or different, are preferably 0 or 1.

y is advantageously equal to 1.

n, p and r, which may be identical or different, are preferably 2 or 3 and even more particularly are equal to 2.

The anion is preferably a halide (chloride, bromide or iodide) or an alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function, may be used.

The anion $X^-$ is even more particularly chloride or methyl sulfate.

The ammonium salts more particularly used are those of formula (VII) in which:

$R_{15}$ denotes a methyl or ethyl radical,
x and y are equal to 1;
z is equal to 0 or 1;
n, p and r are equal to 2;
$R_{16}$ is chosen from:
a radical $$R_{19}-\overset{O}{\underset{\|}{C}}-$$

methyl, ethyl or $C_{14}$-$C_{22}$ hydrocarbon-based radicals;
a hydrogen atom;
$R_{18}$ is chosen from:
a radical $$R_{21}-\overset{O}{\underset{\|}{C}}-$$

a hydrogen atom;

$R_{17}$, $R_{19}$ and $R_{21}$, which may be identical or different, are chosen from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Among the quaternary ammonium salts of formula (IV), the ones that are preferred are, on the one hand, tetraalkylammonium chlorides such as, for example, dialkyldimethylammonium chlorides or alkyltrimethyl-ammonium chlorides, in which the alkyl radical contains from about 12 to 22 carbon atoms, in particular behenyltrimethylammonium chloride, distearyldimethyl-ammonium chloride, cetyltrimethylammonium chloride, or benzyldimethylstearylammonium chloride, or, on the other hand, palmitylamidopropyltrimethylammonium chloride or stearamidopropyldimethyl(myristyl acetate)-ammonium chloride sold under the name Ceraphyl 70 by the company Van Dyk.

Examples of compounds of formula (V) that may be mentioned include the salts (especially chloride or methyl sulfate) of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethylammonium, and mixtures thereof. The acyl radicals preferably contain 14 to 18 carbon atoms and are more particularly derived from a plant oil, for instance palm oil or sunflower oil. When the compound contains several acyl radicals, these radicals may be identical or different.

These products are obtained, for example, by direct esterification of optionally oxyalkylenated triethanolamine, triisopropanolamine, alkyldiethanol-amine or alkyldiisopropanolamine onto fatty acids or onto mixtures of fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart® by the company Cognis, Stepanquat® by the company Stepan, Noxamium® by the company Ceca, and Rewoquat® WE 18 and Rewoquat W75 by the company Degussa.

It is also possible to use the ammonium salts containing at least one ester function described in U.S. Pat. No. 4,874,554 and U.S. Pat. No. 4,137,180.

Diquaternary ammonium salts of formula (VI) that are suitable for use in the invention especially comprise propane tallow diammonium dichloride.

Aqueous Phase

The composition according to the invention comprises an aqueous phase comprising water and/or hydrophilic solvents such as polyols.

The water is preferably present in an amount ranging from 5% to 99% by weight, preferably ranging from 10% to 95% by weight, better still ranging from 20% to 90% by weight and even better still ranging from 30% to 90% by weight relative to the total weight of the composition.

The water used in the composition of the invention may be pure demineralized water, but also mineral water and/or spring water and/or seawater, i.e. the water of the composition may be partly or totally constituted by a water chosen from mineral waters, spring waters or seawater and mixtures thereof. In general, a mineral water is suitable for consumption, which is not always the case for a spring water. Each of these waters contains, inter alia, dissolved minerals and trace elements. These waters are known to be employed for specific treatment purposes according to the particular trace elements and minerals they contain, such as moisturization and desensitization of the skin, or the treatment of certain dermatoses. The terms "mineral water" and "spring water" will denote not only natural mineral or spring waters enriched in additional mineral constituents and/or trace elements, but also aqueous mineral solutions and/or solutions containing trace elements prepared from purified water (demineralized or distilled water).

A natural spring water or mineral water used according to the invention may be chosen, for example, from Vittel water, Vichy basin water, Uriage water, Roche Posay water, Bourboule water, Enghien-les-Bains water, Saint Gervais-les-Bains water, Néris-les-Bains water, Allevar-les-Bains water, Digne water, Maizières water, Neyrac-les-Bains water, Lons-le-Saunier water, Eaux Bonnes water, Rochefort water, Saint Christau water, Fumades water, Tercis-les-bains water and Avene water.

The aqueous phase of the composition of the invention may comprise one or more polyols. Among the polyols that may be used in the composition according to the invention, mention may be made especially of glycerol, propylene glycol, butylene glycol, hexylene glycol, polyethylene glycols such as PEG-8, and dipropylene glycol, and mixtures thereof. According to one preferred embodiment of the invention, the polyol is glycerol, which gives better transparency of the composition than the other polyols. Other polyols may be added to the glycerol, provided that the qualities of the composition and especially the clarity are maintained.

The amount of polyol(s) may range, for example, from 0.5% to 15% by weight, preferably from 0.5% to 10% by weight, better still from 1% to 10% by weight, even better from 2% to 10% by weight and even better still from 2% to 8% by weight relative to the total weight of the composition.

The composition may comprise a hydrophilic gelling agent, preferably chosen from gelling agents of natural origin, in particular of plant origin, or polysaccharides of biotechnological origin (for example xanthan gum).

This plant-derived polysaccharide may, where appropriate, be chemically modified to promote its hydrophilic valency, as is the case for cellulose derivatives, in particular hydroxyalkyl celluloses (e.g.: hydroxyethylcellulose).

As examples of polysaccharides of plant origin that may be used according to the invention, mention may be made especially of:
   a) algal extracts, such as alginates, carrageenans and agars, and mixtures thereof. Examples of carrageenans that may be mentioned include Satiagum UTC30® and UTC10® from the company Degussa; an alginate that may be mentioned is the sodium alginate sold under the name Kelcosol® by the company ISP;
   b) gums, such as guar gum and nonionic derivatives thereof (hydroxypropyl guar), gum arabic, konjac gum or mannan gum, gum tragacanth, ghatti gum, karaya gum or locust bean gum; examples that may be mentioned include the guar gum sold under the name Jaguar HP105® by the company Rhodia; the Mannan and Konjac Gum® (1% gluconomannan) sold by the company GfN;
   c) modified or unmodified starches, such as those obtained, for example, from cereals, for instance wheat, corn or rice, from legumes, for instance blonde pea, from tubers, for instance potato or cassava, and tapioca starches; dextrins, such as corn dextrins; examples that may especially be mentioned include the rice starch Remy DR I® sold by the company Remy; the corn starch B® from the company Roquette; the potato starch modified with 2-chloroethylaminodipropionic acid neutralized with sodium hydroxide, sold under the name Structure Solanace® by the company National Starch; the native tapioca starch powder sold under the name Tapioca Pure® by the company National Starch;
   d) dextrins, such as the dextrin extracted from corn under the name Index® from the company National Starch;
   e) celluloses and derivatives thereof, in particular alkyl celluloses and hydroxyalkyl celluloses; mention may be made especially of methylcelluloses, hydroxyalkylcelluloses, ethyl-hydroxyethylcelluloses and carboxymethyl-celluloses. Examples of cetyl hydroxyethyl-celluloses that may be mentioned include Polysurf 67CS® and Natrosol Plus 330® from Aqualon;

and mixtures thereof.

According to one embodiment, the composition according to the invention comprises less than 1.5% by weight, preferably less than 1% by weight, better still less than 0.5% by weight, or even less than 0.2% by weight of synthetic thickening or gelling polymers. It may be totally free of synthetic thickening or gelling polymers.

Such synthetic polymers are, for example, acrylic polymers (of the Carbopol family), acrylic/alkyl acrylate copolymers or (co)polymers based on 2-acrylamido-2-methylpropanesulfonic acid (for example the polymers sold under the name Pemulen, Sepigel or Simulgel, or Aristoflex).

The compositions of the invention may also contain adjuvants such as those that are common in the cosmetics field, such as antioxidants, preserving agents, dyestuffs, fillers and hydrophilic active agents. The nature of the adjuvants and the amounts thereof should be such that they do not modify the properties of the composition according to the invention. The amounts of these adjuvants are those conventionally used in the cosmetics field, for example from 0.001% to 10% of the total weight of the composition.

As active agents that may be used in the composition of the invention, examples that may be mentioned include calmatives, for instance allantoin and bisabolol; floral waters such as linden tree water or cornflower water; glycyrrhetinic acid and salts thereof; antibacterial agents such as octopirox, triclosan and triclocarban; coenzymes such as coenzyme Q10 or ubiquinone and coenzyme R or biotin; protein hydrolysates; plant extracts and especially plankton extracts; and mixtures thereof.

Needless to say, a person skilled in the art will take care to select the optional additive(s) to be added to the composition according to the invention such that the advantageous properties intrinsically associated with the composition in accordance with the invention are not, or are not substantially, adversely affected by the envisaged addition.

Fillers that may be mentioned include mineral fillers such as talc or magnesium silicate (particle size: 5 microns) sold under the name Luzenac 15 M00® by the company Luzenac, kaolin or aluminium silicate, for instance the product sold under the name Kaolin Supreme® by the company Imerys, or organic fillers such as starch, for instance the product sold under the name Amidon de Maïs B® by the company Roquette, Nylon microspheres, for instance those sold under the name Orgasol 2002 UD NAT COS® by the company Atochem, expanded microspheres based on vinylidene chloride/acrylonitrile/methacrylonitrile copolymer containing isobutane, for instance those sold under the name Expancel 551 DE® by the company Expancel. Fibres may also be added to the composition of the invention, for instance Nylon fibres (Polyamide 0.9 Dtex 0.3 MM sold by the company Etablissements Paul Bonte) and cellulose or "Rayon" fibres (Rayon Flock RCISE NOOO3 MO4® sold by the company Claremont Flock Corporation).

According to one particular embodiment of the invention, the composition according to the invention contains as fillers exfoliant particles, which enable scrubbing of the skin. The exfoliant particles that may be used include exfoliant or scrubbing particles of mineral, plant or organic origin. It is thus possible to use, for example, polyethylene beads or powder, for instance those sold under the name Microthene MN 727 or Microthene MN 710-20 by the company Equistar or the powder sold under the name Gotalene 120 Incolore by the company DuPont; nylon particles, for instance those sold by the company Arkema under the name Orgasol 2002 EXD NAT COS; fibres, for instance polyamide fibres, such as those sold by the company Utexbel under the name Pulpe Polyamide 12185 Taille 0.3 MM; polyvinyl chloride powder; pumice, for instance the pumice 3/B from Eyraud; ground fruit kernel shells such as ground apricot kernels or walnut shells; sawdust; glass beads; alumina (aluminium oxide) (INCI name: alumina), for instance the product sold under the name Dermagrain 900 by the company Marketech International; sugar crystals; beads that melt when applied to the skin, for instance the spheres based on mannitol and cellulose sold under the name Unispheres by the company Induchem, agar-based capsules sold under the name Primasponge by the company Cognis, and spheres based on jojoba esters sold under the name Floraspheres by the company Floratech; and mixtures thereof.

The compositions according to the invention may especially constitute products for cleansing or for removing makeup from keratin materials such as the skin (body, face, eyes, scalp) and/or keratin fibres. The composition may be, for example, a tonic, a foaming facial cleansing cream, a makeup-removing milk, a two-phase or a shampoo.

The composition may be an essentially aqueous composition. It may also be in the form of an emulsion, which may be a water-in-oil (W/O) or oil-in-water (O/W) emulsion, or a multiple emulsion (W/O/W or O/W/O).

According to one particular embodiment, the composition according to the invention is an essentially aqueous composition, comprising, for example, at least 85% by weight of water, preferably at least 90% by weight and better still at least 95% by weight, relative to the total weight of the composition. According to this embodiment, the combination of fatty acid ester of sucrose and fatty acid ester of polyglycerol constitutes the main surfactant system of the composition, as defined hereinabove. In particular, the combination of fatty acid ester of sucrose and fatty acid ester of polyglycerol constitutes the sole surfactant system of the composition, as defined hereinabove.

Another subject of the invention is a process for cleansing or for removing makeup from keratin materials such as the skin, including the scalp, keratin fibres such as the eyelashes or the hair, and/or the lips, wherein a cosmetic composition as defined above is applied to the said keratin materials.

According to one embodiment, this process comprises a step of rinsing the keratin materials with water.

Another subject of the invention consists of the cosmetic use of the composition as defined above, as products for cleansing and/or for removing makeup from keratin materials.

Another subject of the invention consists of a cosmetic process for cleansing keratin materials, wherein the composition of the invention is applied to keratin materials in the presence of water, and the deposit formed and the soiling residues are removed by rinsing with water.

In the case of rinsing the face, the composition according to the invention may constitute a mask, which is rinsed off after a leave-on time of 1 to 3 minutes.

The examples that follow are given as illustrations of the invention and are not limiting in nature. All the amounts are given as weight percentages relative to the total weight of the composition. The names of the compounds are indicated, depending on the case, as the chemical names or the INCI names.

EXAMPLES 1 TO 5

Tonics

|  | Ex. 1 Outside the invention | Ex. 2 Outside the invention | Ex. 3 Outside the invention | Ex. 4 Invention | Ex. 5 Invention |
|---|---|---|---|---|---|
| Phase A |  |  |  |  |  |
| Polyglyceryl-10 laurate (Dermofeel G 10 L from Dr Straetmans) | 2.8 AM | — | 1.4 AM | 1.4 AM | — |
| Polyglyceryl-4 caprate (Tegosoft PC 41 from Evonik) | — | 2.8 AM | 1.4 AM | — | 1.4 AM |

-continued

|  | Ex. 1 Outside the invention | Ex. 2 Outside the invention | Ex. 3 Outside the invention | Ex. 4 Invention | Ex. 5 Invention |
|---|---|---|---|---|---|
| Sucrose laurate (Surfhope SE Cosme C-1216 from Mitsubishi) | — | — | — | 1.4 AM | 1.4 AM |
| Babassu oil (*Orbignya oelifera* seed oil) (Cropure Babassu from Croda) | 0.01 | 0.01 | 0.01 | 0.01 | 0.01 |
| Essential oil of geranium bourbon bio (*Pelargonium graveolens* flower oil) (Sanoflore) Phase B | 0.15 | 0.15 | 0.15 | 0.15 | 0.15 |
| Glycerol | 3 | 3 | 3 | 3 | 3 |
| Sodium benzoate | 0.35 | 0.35 | 0.35 | 0.35 | 0.35 |
| Potassium sorbate | 0.15 | 0.15 | 0.15 | 0.15 | 0.15 |
| Citric acid | qs pH 5.4 | qs pH 5.4 | qs pH 5.4 | qs pH 5.4 | qs pH 5.4 |
| Water | qs 100 | qs 100 | qs 100 | qs 100 | qs 100 |
| Appearance: | Cloudy | Cloudy | Cloudy | Virtually clear (very slightly hazy) | Clear |

AM = Active Materials

Procedure

The ingredients of phase A are mixed together and heated until a uniform mixture is obtained.

The mixture is then added to phase B, the ingredients of which have been premixed at room temperature.

The fatty acid ester of sucrose+fatty acid ester of polyglycerol surfactant system according to the invention allows the production of compositions of clear appearance.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising
   an aqueous phase,
   at least one lipophilic compound selected from the group consisting of an essential oil, and an oil of plant origin selected from group consisting of liquid triglycerides of fatty acids of 4 to 30 carbon atoms, jojoba oil, babassu oil, sunflower oil, olive oil, coconut oil, brazil nut oil, marula oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, in a content of 0.05 to 1% by weight relative to the total weight of the composition, and
   a surfactant system comprising a combination of at least one fatty acid ester of sucrose and of at least one fatty acid ester of polyglycerol,
   the ratio of fatty acid ester of sucrose to fatty acid ester of polyglycerol being greater than or equal to 0.06,
   wherein the aqueous phase comprises at least one polyol in an amount of from 0.5 to 15% by weight, relative to the total weight of the composition.

2. The composition according to claim 1, wherein the fatty acid ester of sucrose is an ester derived from the reaction of sucrose(s) and of fatty acid(s) containing from 10 to 24 carbon atoms.

3. The composition according to claim 2, wherein the fatty acid is selected from the group consisting of oleic acid, lauric acid, palmitic acid, myristic acid, stearic acid, linoleic acid, capric acid, and mixtures thereof.

4. The composition according to claim 1, wherein the fatty acid ester of sucrose is an ester derived from the reaction of sucrose and of a fatty acid containing from 12 to 18 carbon atoms.

5. The composition according to claim 1, wherein the fatty acid ester of sucrose is selected from the group consisting of sucrose laurate, sucrose palmitate, and a mixture thereof.

6. The composition according to claim 1, wherein the amount of fatty acid ester(s) of sucrose is 0.1% to 20% by weight relative to the total weight of the composition.

7. The composition according to claim 1, wherein the fatty acid ester of polyglycerol is an ester derived from the reaction of polyglycerol comprising from 2 to 12 glycerol units and of at least one fatty acid containing from 8 to 24 carbon atoms.

8. The composition according to claim 7, wherein the fatty acid is selected from the group consisting of oleic acid, stearic acid, isostearic acid, lauric acid, palmitic acid, myristic acid, linoleic acid, capric acid, caprylic acid, and mixtures thereof.

9. The composition according to claim 1, wherein the fatty acid ester of polyglycerol is an ester derived from the reaction of polyglycerol comprising from 2 to 12 glycerol units and of at least one fatty acid comprising less than 16 carbon atoms.

10. The composition according to claim 1, wherein the fatty acid ester of polyglycerol is an ester derived from the reaction of polyglycerol comprising from 4 to 10 glycerol units and of at least one fatty acid containing from 8 to 12 carbon atoms.

11. The composition according to claim 1, wherein the fatty acid ester of polyglycerol is selected from the group consisting of an ester derived from the reaction of polyglycerol-10 and lauric acid, an ester derived from the reaction of polyglycerol-4 and capric acid, and mixtures thereof.

12. The composition according to claim 1, wherein the fatty acid ester of polyglycerol is present in an amount of 0.1% to 20% by weight relative to the total weight of the composition.

13. The composition according to claim 1, wherein the ratio of fatty acid ester of sucrose to fatty acid ester of polyglycerol is greater than or equal to 0.5.

14. The composition according to claim 1, wherein the ratio of fatty acid ester of sucrose to fatty acid ester of polyglycerol is 0.6-1.4.

15. A process for cleansing or for removing makeup from a keratin material, comprising applying a composition according to claim 1 to said keratin material.

16. The composition according to claim 1, wherein the fatty acid ester of sucrose is an ester derived from the reaction of sucrose and of a fatty acid containing from 18 to 24 carbon atoms.

17. The composition according to claim 1, wherein the composition is an aqueous composition.

18. The composition according to claim 1, which is clear and stable.

* * * * *